United States Patent [19]
Smith

[11] Patent Number: 6,083,202
[45] Date of Patent: Jul. 4, 2000

[54] ENDOSCOPIC NEEDLE INJECTION DEVICE

[75] Inventor: Kevin W. Smith, Coral Gables, Fla.

[73] Assignee: Syntheon, LLC, Miami, Fla.

[21] Appl. No.: 09/418,245

[22] Filed: Oct. 14, 1999

[51] Int. Cl.[7] .................................................. A61M 5/00
[52] U.S. Cl. .............................................. 604/164; 604/169
[58] Field of Search .................................. 604/164, 158, 604/159, 165, 236, 198, 169

[56] References Cited

U.S. PATENT DOCUMENTS

| | | | |
|---|---|---|---|
| 5,562,634 | 10/1996 | Flumene et al. | 604/164 X |
| 5,573,510 | 11/1996 | Isaacson | 604/158 |
| 5,601,533 | 2/1997 | Hancke et al. | 604/164 |
| 5,601,588 | 2/1997 | Tonomura et al. | 606/185 |
| 5,817,058 | 10/1998 | Shaw | 604/164 X |
| 5,911,705 | 6/1999 | Howell | 604/164 X |
| 5,954,698 | 9/1999 | Pike | 604/169 |
| 5,961,493 | 10/1999 | Liu | 604/164 |

*Primary Examiner*—John D. Yasko
*Attorney, Agent, or Firm*—David P. Gordon; David S. Jacobson; Thomas A. Gallagher

[57] ABSTRACT

An endoscopic injection needle includes a flexible inner tube having a needle attached at a distal end thereof, a flexible outer jacket extending over the inner tube, and a handle assembly attached to the proximal ends of the inner tube and jacket to move the needle at the distal end of the inner tube relative to the distal end of the jacket. The handle assembly is adapted to be attached firmly to the handle of the endoscope via an attachment. To advance and withdraw the outer jacket, the physician moves a sliding component of the handle assembly, which is connected to the jacket. By moving the sliding component proximally and distally relative to the rest of the handle assembly, the jacket is advanced and withdrawn from the distal end of the endoscope. Once the desired position is achieved for the jacket, the position of the jacket relative to the endoscope can be fixed. After the jacket has been positioned, the physician moves the needle distally relative to the jacket and into the tissue by operating a piston portion of the handle assembly. Further movement of the piston portion of the handle assembly injects fluid from a reservoir in the handle assembly through the inner tubular member and needle, and into the tissue. Hence, the physician has full control of the procedure and does not require the services of an assistant to accomplish the injections.

33 Claims, 2 Drawing Sheets

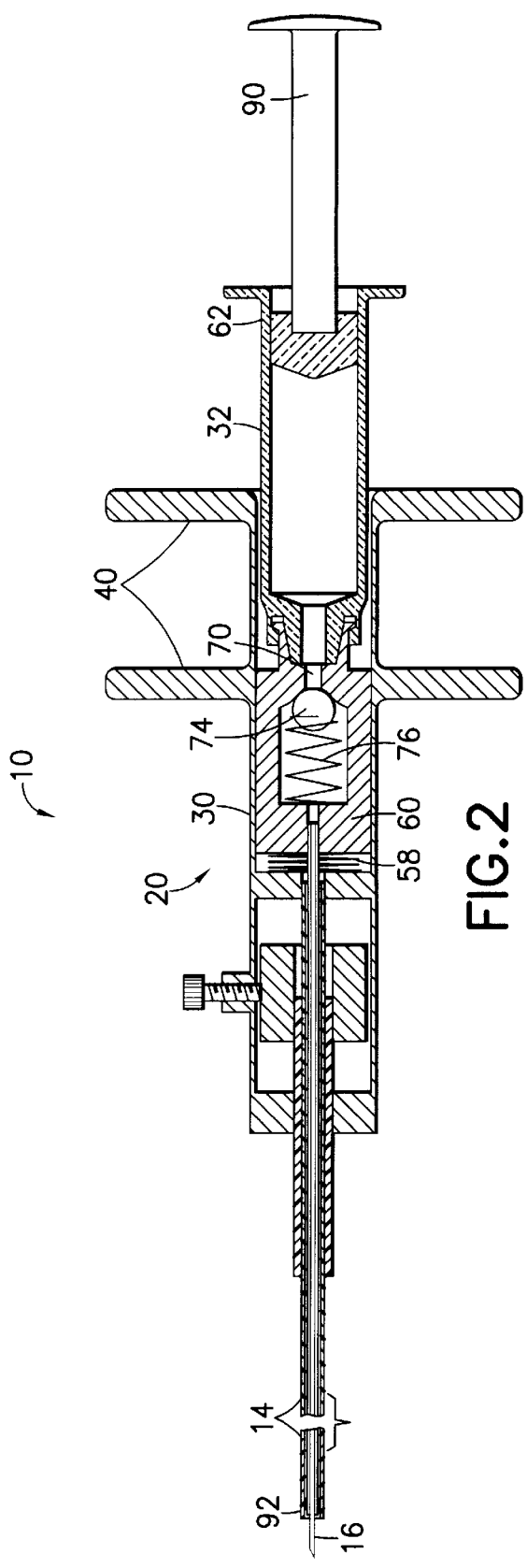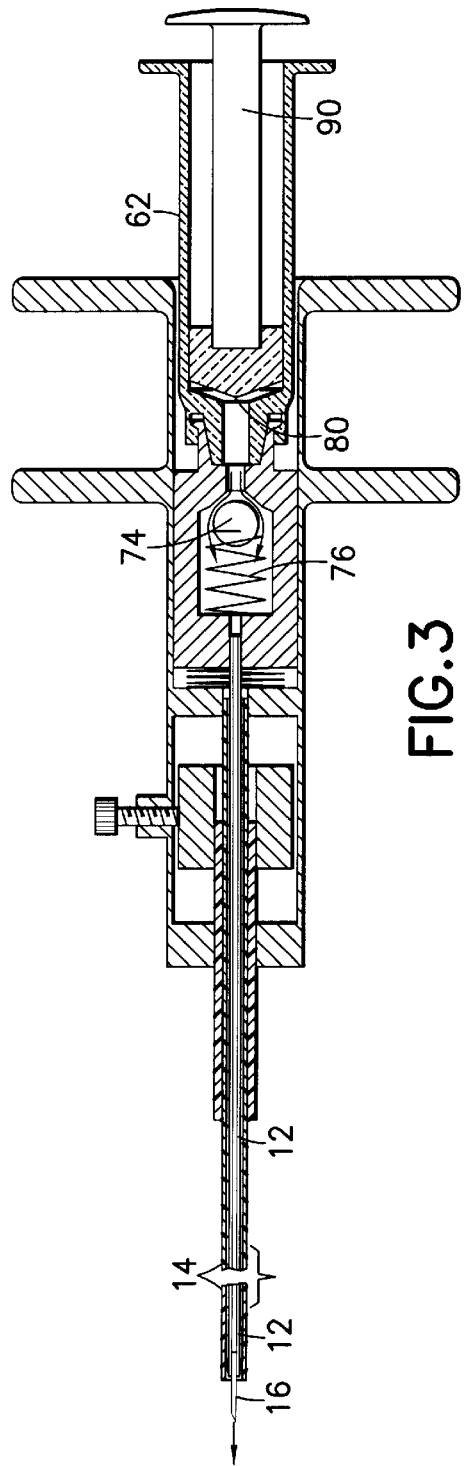

ENDOSCOPIC NEEDLE INJECTION DEVICE

BACKGROUND OF THE INVENTION

1. Field of the Invention

This invention relates broadly to surgical instruments. More particularly, this invention relates to endoscopic injection needle devices insertable into an endoscope.

2. State of the Art

An endoscopic injection needle is inserted through a lumen of a flexible endoscope to inject fluids under endoscopic visualization in such body structures as the esophagus, the colon, and the stomach. For example, during a colonic polypectomy, it is customary to inject saline solution into the tissue surrounding and underlying a polyp in order to "raise" the polyp to facilitate excision of the polyp by means of an endoscopic forceps or snares. Also, visible dyes and radiological contrast dyes are sometimes injected to mark the location of areas explored endoscopically so that the structures can be located during subsequent procedures. Additionally, sclerosing agents are sometimes injected into vascular structures, such as esophageal varicoceles, in order to cause clotting and to necrose the tissue so that it can be resorbed by the body.

The current art consists of several endoscopic needles marketed by companies such as Boston Scientific/Microvasive, Olympus, Wilson-Cook and others. Typically, the needle devices generally consist of an inner flexible tubing, usually made of polytetrafluoroethylene (PTFE), surrounded by a loose-fitting outer jacket made of PTFE, fluorinated ethylene propylene (FEP), or similar flexible plastic, a handle assembly at the proximal ends of the inner tubing and outer jacket, and a needle attached to the distal end of the inner tubing. A physician grips the outer jacket of the needle device with one hand to introduce it through a sealing port on the endoscope handle which communicates with the working channel of the endoscope and to position the distal end of the device proximate the desired tissue at the distal end of the endoscope. With his or her other hand, the physician holds the proximal handle of the endoscope so that the steering knobs on the endoscope handle can manipulated while viewing the endoscope image. The handle assembly of the endoscopic needle device is held and manipulated by an assistant, according to the oral commands of the physician. For example, the physician may manipulate the knobs of the endoscope to position the tip of the endoscope near (within a few millimeters of) a polyp. The physician then advances the outer jacket of the needle device into the endoscope handle until the distal end of the outer jacket approaches and touches the tissue surrounding the polyp. Then the physician orders the assistant to advance the needle, which the assistant does by operating a needle-advance function on the handle assembly of the needle device. Then the physician orders the assistant to inject fluid, which the assistant does by operating a syringe connected to the handle assembly of the needle device. The physician then orders the assistant to stop injecting and withdraw the needle. These operations complete one injection; typically, the physician injects several times around a polyp in order to achieve the desired results. Accordingly, the procedure takes a great deal of time and requires precise coordination between physician and assistant.

SUMMARY OF THE INVENTION

It is therefore an object of the invention to provide an endoscopic injection needle device which requires less coordination between the physician and the assistant.

It is another object of the invention to provide an endoscopic injection needle device which permits the physician to directly control more functionality of an endoscopic injection needle device.

It is a further object of the invention to provide an endoscopic injection needle device which permits the physician to directly control the motion of the needle jacket as well as the motion of the needle.

In accord with these objects, which will be discussed in detail below, an endoscopic injection needle device is provided which includes a flexible inner tube having a needle attached at a distal end thereof, a flexible outer jacket extending over the inner tube, and a handle assembly attached to the proximal ends of the inner tube and outer jacket. The handle assembly is adapted to move the needle at the distal end of the inner tube relative to the distal end of the outer jacket, to inject fluid through the inner tube and the needle, and to adjustably and removably couple the needle device to an endoscope. The handle assembly is further adapted to be attached firmly to the handle of the endoscope via an attachment, such as a short, stiff tubing at the distal end of the handle assembly which extends over a proximal portion of the outer jacket of the needle device and tightly couples to the sealing valve on the endoscope handle. Once pushed into the sealing valve, the stiff tubular extension serves to join the handle assembly of the needle device to the endoscope handle during the procedure. Then, to advance and withdraw the outer jacket, the physician moves a sliding component of the handle assembly, which is connected to the outer jacket. Once the desired position is achieved for the outer jacket, the position of the jacket relative to the endoscope can be fixed. After the outer jacket has been positioned and fixed, the physician moves the needle distally relative to the outer jacket and into the tissue by moving a plunger portion of the handle assembly a predetermined distance relative to the rest of the handle assembly. Further movement of the plunger portion of the handle assembly injects fluid from a reservoir in the handle assembly through a valve, the inner tube and the needle, and into the tissue. Hence, the physician has full control of the procedure and does not require the services of an assistant to accomplish the injections. In this manner, it is possible to perform many injections quickly, efficiently, and accurately, because there is no need for communication and coordination with an assistant.

Additional objects and advantages of the invention will become apparent to those skilled in the art upon reference to the detailed description taken in conjunction with the provided figures.

BRIEF DESCRIPTION OF THE DRAWINGS

FIG. 2 is a partial broken side elevation of the needle injection device according to the invention where the needle is in a pre-injection needle extended position; and FIG. 3 is a partial broken side elevation of the needle injection device according to the invention where the syringe is in a post-injection compressed position.

DETAILED DESCRIPTION OF THE PREFERRED EMBODIMENTS

Figure 1:
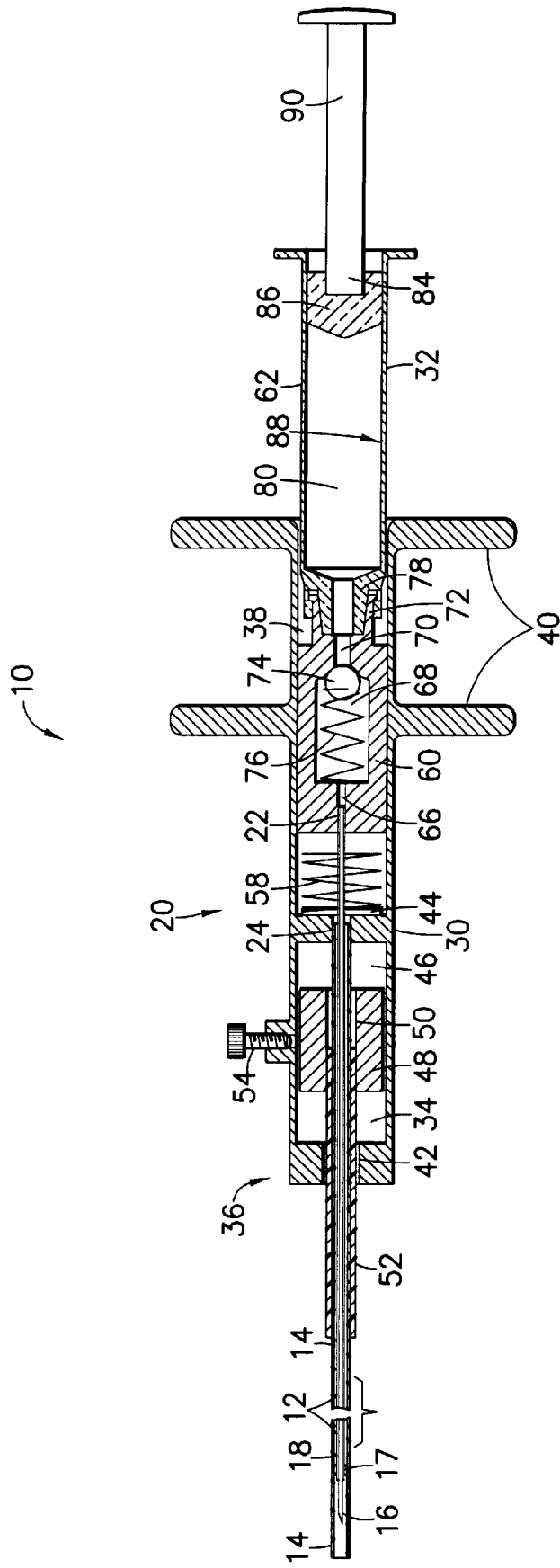
FIG. 1 is a partial broken side elevation of the endoscopic needle injection device according to the invention where the needle is in a withdrawn position.

Turning now to FIG. 1, an endoscopic needle injection device 10 according to the invention is shown. The endoscopic needle injection device 10 includes a flexible inner tubular member 12, which is designed to be approximately the same length as a typical endoscope, a flexible outer sheath 14 extending over the inner tubular member 12, an injection needle 16 attached, e.g., by a crimped band 17, to the distal end 18 of the inner tubular member 12 such that both are in fluid communication, and a proximal handle assembly 20 coupled to the proximal ends 22, 24 of the inner tubular member 12 and outer sheath 14. The handle assembly 20, as described in more detail below, is adapted to move the inner tubular member 12 relative to the outer sheath 14, to be coupled to an endoscope, to adjust the longitudinal position of the outer sheath 14 relative to the endoscope, and to inject fluid through the inner tubular member 12 and the needle 16. The inner tubular member 12 and outer sheath 14 are preferably made from PTFE, FEP, or a similar plastic, and the needle is preferably manufactured from stainless steel. However, other materials for each may be used, and the inner tubular member 12 and needle 16 may be formed together from a single piece of material.

The handle assembly 20 has a distal stationary portion 30 and a proximal movable portion 32 movable relative to the stationary portion. The stationary portion 30 includes a stepped bore 34, an endoscope coupling assembly 36 which is adapted to couple the handle assembly 20 to a port (sealing valve) of an endoscope, a proximal opening 38 in which the movable portion 32 is slidably provided, and a toroidal finger grip 40. The stepped bore 34 includes a distal portion 42, a proximal portion 44, and a relatively large central portion 46. The proximal end 24 of the outer jacket 14 is fixedly coupled within the proximal portion 44 of the stepped bore 34.

The coupling assembly 36 includes a cylindrical block 48 having an axial bore 50 and axially slidable within the central portion 46 of the stepped bore 34, and a preferably stiff tubular nosepiece 52. The nosepiece 52 extends over the outer sheath 14, and is movable relative thereover and into the distal and central portions 42, 46 of the stepped bore 34. The nosepiece 52 is fixedly coupled within the axial bore 50 of the block 48 such that movement of the block within the stepped bore 34 causes movement of the nosepiece 52. The nosepiece 52 is preferably made from a 3.2 mm diameter and 25 mm long section of tubular stainless steel, although other diameters, lengths, and materials may be used. A locking screw 54 extends radially into the central portion 46 of the stepped bore 34 of the stationary portion 30 such that the screw 54 may be rotated to tighten against the block 48 and nosepiece 52 and lock the block relative to the stationary portion 30.

The movable portion 32 of the handle assembly 20 includes a valve assembly 60 and a syringe assembly 62. The movable portion 32 is slidably positioned within the proximal opening 38 of the stationary member 30, with a first spring 58 (also called the 'needle spring') provided in the proximal opening 38 between the valve assembly 60 and the proximal portion 44 of the stepped bore 34 of the stationary member 30. The valve assembly 60 includes a distal opening 66 in which the proximal end 22 of the inner tubular member 12 is fixed, a proximal opening 70 partially defined by a female luer connector 72, a central chamber 68 in fluid communication with the distal and proximal openings 66, 70, a ball 74 within the chamber 68, and a second spring 76 (also called a 'valve spring') within the chamber which forces the ball 74 to obstruct the proximal opening 70. The syringe assembly 62 includes a distal male luer connector 78 which is removably coupled to the female luer connector 72 of the valve assembly 60, a reservoir 80, and a piston member (plunger) 84. The piston member 84 preferably includes a resilient plunger portion 86 which makes fluid-tight contact with the interior surface 88 of the reservoir 80, and a thumb-operable handle portion 90. The piston member 84 is manually slidable within the reservoir 80 to pressurize fluid within the reservoir 80 and force the fluid through the luer connectors 72, 78, moving the ball 74 against the valve spring 76 such that the fluid is forced into the distal opening 66 of the valve assembly 60 and through the tubular member 12 to the needle 16.

In use, the syringe assembly 62 of movable portion 32 of the handle assembly 20 is removed from the handle assembly by uncoupling the luer connectors 72, 78. The reservoir 80 of the syringe assembly 62 is then at least partially filled with a desired fluid or medicament, and the syringe assembly 62 is preferably recoupled to the handle assembly 20.

The distal end of the endoscopic injection needle device 10 is fed through a sealing valve on an endoscope and through and beyond the working channel of the endoscope until the nosepiece 52 is forced into the sealing valve of the endoscope and joins the handle assembly 20 firmly to the endoscope handle. The position of the distal end of the outer jacket 14 relative to the distal end of the endoscope may be set by the physician by loosening the set screw 54 and sliding the stationary portion 30 relative the nosepiece 52, as the nosepiece is coupled to the endoscope and the proximal end 22 of the outer jacket is coupled to the stationary portion 30. Once the desired relative positions of the handle assembly 20 and the nosepiece 52 are obtained, the physician tightens the set screw 54 to fix their relative positions.

Turning now to FIG. 2, once the outer jacket 14 of the needle injection device 10 has been positioned, the physician is then able to move the needle 16 distally relative to the outer jacket 14 and into the tissue. In particular, the physician places two of his or her fingers within the finger grip 40 and pushes on the handle portion 90 of the piston member 84 with the thumb to apply relative force between the stationary and movable portions 30, 32 of the handle assembly 20. The spring constants of the needle spring 58 and valve spring 76 are preferably chosen so that the needle spring 58 completely compresses prior to opening of the valve assembly 60. For example, the needle spring 58 may be designed to be entirely compressed by a force of one pound, while the valve spring 76 may be designed to be at least partially compressed by a force of two pounds, such that with two pounds of pressure, the ball 74 may be moved from the proximal opening 70 to permit fluid to pass therethrough. Thus, when a force of one pound is applied to the piston member 84, the needle spring 58 completely compresses, allowing the needle 16 to advance to its distal-most position, beyond the distal end 92 of the outer jacket 14, but no fluid is released from the syringe assembly 62.

Alternatively, the needle spring 58 and the valve spring 76 may have the same spring constants, with the valve spring being preloaded; i.e., partially compressed, to an extent greater than the needle spring. Moreover, the needle spring 76 may even have a higher spring constant than the needle spring 58, but the valve spring may be sufficiently preloaded to prevent compression until the needle spring is compressed. In either case, the needle spring 58 completely compresses prior to opening of the valve assembly 60.

In any case, when the needle moves to its distalmost position, the physician feels that there is no further motion even as he or she pushes slightly harder on the piston, and this cessation of movement signals to the physician that the needle is fully extended and in the tissue.

Referring now to FIG. 3, once the needle 16 is positioned in the tissue, the physician increases the force on the piston member 84 to a sufficient level, e.g., two pounds, to cause the fluid pressure in the reservoir 80 of the syringe assembly 62 to overcome the force of the valve spring 76. At that point, fluid begins to flow from the syringe assembly around the ball 74 and into the inner tubular member 12, and then into the tissue. Once the desired amount of fluid has been injected at that site, the physician releases pressure on the piston 90, causing the fluid injection to cease, and causing the needle 16 to retract into the outer jacket 14. The endoscope can then be moved so that the needle is repositioned, and the entire sequence can then be repeated as long as fluid remains in the reservoir 80 of the syringe assembly 62.

As such, the physician has full control of the procedure and does not require the services of an assistant to accomplish the injections. In this manner, it is possible to perform many injections quickly, efficiently, and accurately, because there is no need for communication and coordination with an assistant.

There has been described and illustrated herein a preferred embodiment of an endoscopic needle injection device. While a particular embodiment of the invention have been described, it is not intended that the invention be limited thereto, as it is intended that the invention be as broad in scope as the art will allow and that the specification be read likewise. Thus, while a particular nosepiece adapted to couple to the sealing valve of the endoscope has been disclosed, it will be appreciated that other coupling devices may be used as well. For example, a threaded attachment having either internal or external threads may be provided which threadably couples to or about the sealing valve. Also, while a coil-type spring has been shown for both the needle spring and the valve spring, it will be appreciated that another resilient device may be used in place of the coil spring. For example, non-coiled resilient members, compressible plastic or rubber elements may be used. In addition, while a particular valve has been disclosed, it will be appreciated that other valve assemblies may be used. Furthermore, while a particular handle assembly has been disclosed for moving the needle relative to the jacket and injecting fluid through the needle, it will be understood that a handle assembly with a different configuration, e.g., a trigger-type handle assembly, may be adapted to perform the same function. Moreover, while a screw has been disclosed to fix the block and nosepiece relative to the stationary portion of the handle assembly, it will be appreciated that the sliding motion of the nosepiece relative to the endoscope may be arranged with a frictional arrangement (a detent) or other fixing means in order that the jacket can be easily moved by the physician, yet is held in place sufficiently well that it is unlikely to be moved inadvertently. In addition, while a spring-biased valve has been disclosed, it will be appreciated that other valves may likewise be used. Furthermore, while the injection device has been disclosed primarily for use through an endoscope, it will be appreciated that the injection device may be used (1) within a guiding catheter, e.g., moved through a guiding catheter positioned into the catheter for application of gene therapy, (2) within a hemostasis sheath; i.e., a sheath of the type utilized to create an entry port into an artery or vein, or (3) within any other elongate flexible member to provide a medically useful application, each such member having a proximal end or handle having an entry port to which the needle device may be coupled, and a working channel or lumen therethrough. It will therefore be appreciated by those skilled in the art that yet other modifications could be made to the provided invention without deviating from its spirit and scope as claimed.

What is claimed is:

1. An injection needle device for injecting a fluid and for insertion through an elongate medical device having a lumen with a distal end and a proximal port in fluid communication with the lumen, said injection needle device comprising:
   a) a first tubular member having proximal and distal ends;
   b) a needle at the distal end of said first tubular member;
   c) a second tubular member having proximal and distal ends and extending over said first tubular member; and
   d) a proximal handle assembly coupled to said proximal ends of said first and second tubular members and including,
      i) coupling means for coupling said injection needle device to the medical device such that said distal ends of said first and second tubular members extend at least partially through the lumen of the medical device,
      ii) adjusting means for adjustably fixing said distal end of said second tubular member relative to the distal end of the lumen of the medical device,
      iii) moving means for moving said first and second tubular members relative to each other, and
      iv) injecting means for injecting the fluid through said first tubular member and said needle.

2. An injection needle device according to claim 1, wherein:
   said coupling means comprises a substantially stiff tubular element dimensioned to be inserted into and stably held in the proximal port of the medical device.

3. An injection needle device according to claim 1, wherein:
   said handle assembly includes a stationary portion and a movable portion movable relative to said stationary portion, said first tubular member being coupled to said movable portion, and said second tubular member being coupled to said stationary portion.

4. An injection needle device according to claim 3, wherein:
   said stationary portion includes a bore having a sliding member provided therein, and a fixing means for longitudinally fixing said sliding member within said bore, said coupling means being fixedly attached to said sliding member.

5. An injection needle device according to claim 4, wherein:
   said fixing means includes a set screw.

6. An injection needle device according to claim 3, wherein:
   said handle assembly further includes a spring interposed between said stationary portion and said movable portion, wherein movement of said movable member axially toward said stationary member requires that sufficient relative force be provided to said stationary and movable portions to overcome a spring constant of said spring.

7. An injection needle device according to claim 3, wherein:
   said movable portion includes said injecting means and a valve assembly, wherein when said valve assembly is in an open position said valve assembly is in fluid communication with said injecting means such that fluid injected by said injecting means is capable of passing through said valve assembly.

8. An injection needle device according to claim 7, wherein:
said valve assembly includes a valve spring biases said valve assembly in a closed position.

9. An injection needle device according to claim 8, wherein:
said handle assembly further includes a second spring interposed between said stationary portion and said movable portion, wherein movement of said movable member axially toward said stationary member requires that sufficient relative force be provided to said stationary and movable portions to compress said second spring, a force required to compress said valve spring is greater than said force required to compress said second spring.

10. An injection needle device according to claim 3, wherein:
a proximal portion of said valve assembly includes a first luer connector and a distal portion of said injecting means includes a second luer connector couplable to said first luer connector such that said valve assembly and said injection means are removably couplable together.

11. An injection needle device according to claim 3, wherein:
said stationary portion includes a finger grip and said injecting means of said movable portion includes a reservoir portion adapted to receive a fluid and a piston axially movable within said reservoir to pressurize the fluid,
wherein when said piston is moved a predetermined distance distally towards said finger grip, said movable portion is moved distally relative to said stationary member such that said first tubular member and said needle at said distal end thereof is moved distally relative to said second tubular member, and when said piston is moved further than said predetermined distance, fluid in said reservoir portion is injected through said first tubular member and said needle.

12. An injection needle device according to claim 1, wherein:
said first tubular member and said needle are discretely formed and coupled together.

13. An injection needle device for injecting a fluid and for insertion through an elongate medical device having a lumen with a distal end and a proximal port in fluid communication with the lumen, said endoscopic needle injection device comprising:
a) a first tubular member having proximal and distal ends;
b) a needle at the distal end of said first tubular member;
c) a second tubular member having proximal and distal ends and extending over said first tubular member; and
d) a proximal handle assembly coupled to said proximal ends of said first and second tubular members and including,
i) moving means for moving said first and second tubular members relative to each other,
ii) injecting means for injecting the fluid through said first tubular member and said needle, and
iii) a valve assembly which when closed prevents passage of the fluid between said injecting means and said first tubular member, and which when open permits passage of the fluid between said injecting means and said first tubular member.

14. An injection needle device according to claim 13, wherein:
said handle assembly includes a stationary portion and a movable portion movable relative to said stationary portion, said first tubular member being coupled to said movable portion, and said second tubular member being coupled to said stationary portion.

15. An injection needle device according to claim 14, wherein:
said handle assembly further includes a spring interposed between said stationary portion and said movable portion, wherein movement of said movable member axially toward said stationary member requires that sufficient relative force be provided to said stationary and movable portions to overcome a spring constant of said spring.

16. An injection needle device according to claim 13, wherein:
said valve assembly includes a valve spring which biases said valve assembly in a closed position.

17. An injection needle device according to claim 16, wherein:
said handle assembly further includes a second spring interposed between said stationary portion and said movable portion, wherein movement of said movable member axially toward said stationary member requires that sufficient relative force be provided to said stationary and movable portions to compress said second spring, wherein said force required to compress said second spring is less than a force required to compress said valve spring.

18. An injection needle device according to claim 13, wherein:
a proximal portion of said valve assembly includes a first luer connector and a distal portion of said injecting means includes a second luer connector couplable to said first luer connector such that said valve assembly and said injection are removably couplable together.

19. An injection needle device according to claim 14, wherein:
said stationary portion includes a finger grip and said injecting means of said movable portion includes a reservoir portion adapted to receive a fluid and a piston axially movable within said reservoir,
wherein when said piston is moved a predetermined distance distally towards said finger grip, said movable portion is moved distally relative to said stationary member such that said first tubular member and said needle at said distal end thereof is moved distally relative to said second tubular member, and when said piston is moved further than said predetermined distance, fluid in said reservoir portion is injected through said first tubular member and said needle.

20. An injection needle device according to claim 13, wherein:
said handle assembly further includes,
iii) coupling means for coupling said needle injection device to the medical device such that said distal ends of said first and second tubular members extend at least partially through the lumen of the medical device, and
iv) adjusting means for adjustably fixing said distal end of said second tubular member relative to the distal end of the lumen.

21. An injection needle device according to claim 13, wherein:
said first tubular member and said needle are discretely formed and coupled together.

22. An injection needle device for injecting a fluid and for insertion through an elongate medical device having a lumen with a distal end and a proximal port in fluid communication with the lumen, said needle injection device comprising:
   a) a first tubular member having proximal and distal end;
   b) a needle at the distal end of said tubular member;
   c) a second tubular member having proximal and distal ends and extending over said first flexible tubular member; and
   d) a proximal handle assembly including a stationary portion coupled to one of said first and second tubular members and a movable portion coupled to the other of said first and second tubular members, wherein movement of said movable portion relative to said stationary portion moves said first and second tubular members relative to each other, said stationary portion including a bore, a sliding member provided in said bore and axially movable therein, a fixing means for longitudinally fixing said sliding member within said bore, and a coupling means fixedly coupled to said sliding member for coupling said stationary member relative to the port of the medical device.

23. An injection needle device according to claim 22, wherein:
   said handle assembly further includes a first spring interposed between said stationary portion and said movable portion, wherein movement of said movable member axially toward said stationary member requires that sufficient relative force be provided to said stationary and movable portions to overcome a spring constant of said first spring.

24. An injection needle device according to claim 22, wherein:
   said movable portion includes an injecting means for injecting a fluid through said first tubular member and said needle, and a valve assembly, wherein when said valve assembly is in an open position said valve assembly is in fluid communication with said injecting means such that fluid injected by said injecting means is capable of passing through said valve assembly.

25. An injection needle device according to claim 24, wherein:
   said valve assembly includes a valve spring which biases said valve assembly in a closed position.

26. An injection needle device according to claim 25, wherein:
   said handle assembly further includes a second spring interposed between said stationary portion and said movable portion, wherein movement of said movable member axially toward said stationary member requires that sufficient relative force be provided to said stationary and movable portions to compress said second spring, wherein said force required to compress said second spring is less than a force required to compress said valve spring.

27. An injection needle device according to claim 26, wherein:
   said stationary portion includes a finger grip and said injecting means of said movable portion includes a reservoir portion adapted to receive a fluid and a piston axially movable within said reservoir,
   wherein when said piston is moved a predetermined distance distally towards said finger grip, said movable portion is moved distally relative to said stationary member such that said first tubular member and said needle at said distal end thereof is moved distally relative to said second tubular member, and when said piston is moved further than said predetermined distance, fluid in said reservoir portion is injected through said first tubular member and said needle.

28. An injection needle device according to claim 23, wherein:
   a proximal portion of said valve assembly includes a first luer connector and a distal portion of said injecting means includes a second luer connector couplable to said first luer connector such that said valve assembly and said injection are removably couplable together.

29. An injection needle device according to claim 23, wherein:
   said first tubular member and said needle are discretely formed and coupled together.

30. An injection needle device, comprising:
   a) a first tubular member having proximal and distal ends;
   b) a needle at the distal end of said first tubular member;
   c) a second tubular member having proximal and distal ends and extending over said first flexible tubular member; and
   d) a proximal handle assembly coupled to said proximal ends of said first and second tubular members and including,
      i) moving means for moving said needle and said end of said second tubular member relative to each other, said moving means including a first spring means requiring a first force for compression thereof and for providing resistance to relative movement of said first and second tubular members which causes said needle to extend beyond said distal end of said second tubular member, and
      ii) injecting means for injecting a fluid through said first tubular member and said needle, and including a valve having a second spring means requiring a second force for compression thereof and for resisting opening of said valve, said second force being greater than said first force.

31. An injection needle device according to claim 30, wherein:
   said handle assembly further includes,
      iii) coupling means for coupling said injection needle device to a medical device having a lumen provided with a distal end such that said distal ends of said first and second tubular members extend at least partially through the lumen, and
      iv) adjusting means for adjustably fixing said distal end of said second tubular member relative to the distal end of the lumen.

32. An injection needle device for injecting a fluid and for insertion through an elongate medical device having a lumen with a distal end and a port in fluid communication with the lumen, injection needle device comprising:
   a) a first tubular member having proximal and distal ends;
   b) a needle at the distal end of said first tubular member;
   c) a second tubular member having proximal and distal ends and extending over said first tubular member; and
   d) a proximal handle assembly coupled to said proximal ends of said first and second tubular members and operable to move said first and second tubular members relative to each other, said handle assembly defining a bore and further including,
      a distal element adapted to be attached to or about the port of the medical device such that said distal ends of said first and second tubular members extend at least partially through the lumen, a sliding member provided in said bore, a fixing means for longitudinally fixing said sliding member within said bore, said distal element being fixedly attached to said sliding member, and a syringe adapted to inject the fluid through said first tubular member and said needle.

33. An injection needle device, comprising:
a) a first tubular member having proximal and distal ends;
b) a needle at the distal end of said first tubular member;
c) a second tubular member having proximal and distal ends and extending over said first tubular member; and
d) a proximal handle assembly coupled to said proximal ends of said first and second tubular members and including,
   i) a first handle portion coupled to one of said first and second tubular members,
   ii) a second handle portion coupled to the other of said first and second tubular members and movable relative to said first handle portion such that relative movement of said first and second handle portions causes relative movement of said first and second tubular members,
   iii) a syringe adapted to inject the fluid through said first tubular member and said needle, and
   iv) a valve assembly interposed between said syringe and said first tubular member such that when said valve assembly is closed, said valve assembly prevents passage of the fluid between said syringe and said first tubular member, and when said valve assembly is open, said valve assembly permits passage of the fluid between said syringe and said first tubular member.

\* \* \* \* \*